(12) United States Patent
Inoue et al.

(10) Patent No.: US 7,381,314 B2
(45) Date of Patent: Jun. 3, 2008

(54) LIQUID ELECTROCHEMICAL GAS SENSOR

(75) Inventors: Tomohiro Inoue, Minoo (JP); Yuki Fujimori, Minoo (JP)

(73) Assignee: Figaro Engineering Inc., Minoo-shi, Osaka (JP)

( * ) Notice: Subject to any disclaimer, the term of this patent is extended or adjusted under 35 U.S.C. 154(b) by 449 days.

(21) Appl. No.: 11/093,207

(22) Filed: Mar. 30, 2005

(65) Prior Publication Data

US 2006/0196770 A1    Sep. 7, 2006

(30) Foreign Application Priority Data

Mar. 4, 2005    (JP) .............................. 2005-060747

(51) Int. Cl.
*G01N 27/403*    (2006.01)

(52) U.S. Cl. ........................ 204/431; 204/430; 204/432

(58) Field of Classification Search ................ 204/430, 204/431, 432, 409; 429/29, 46, 303
See application file for complete search history.

(56) References Cited

U.S. PATENT DOCUMENTS

| 2,870,067 | A | * | 1/1959 | Baker et al. ............. 205/779.5 |
| 3,305,469 | A | * | 2/1967 | Poulos ....................... 204/431 |
| 3,470,071 | A | * | 9/1969 | Oswin et al. ............ 205/779.5 |
| 3,607,426 | A | * | 9/1971 | Niedrach ....................... 429/42 |
| 4,587,003 | A |   | 5/1986 | Tantram et al. |
| 4,820,386 | A |   | 4/1989 | LaConti et al. |
| 5,126,035 | A |   | 6/1992 | Kiesele et al. |
| 5,240,893 | A |   | 8/1993 | Witherspoon |
| 5,302,274 | A |   | 4/1994 | Tomantschger et al. |
| 5,650,054 | A |   | 7/1997 | Shen et al. |
| 5,958,200 | A |   | 9/1999 | Kessel |
| 6,080,294 | A | * | 6/2000 | Shen et al. ................. 204/415 |
| 6,096,453 | A | * | 8/2000 | Grunwald .................... 429/212 |
| 6,200,443 | B1 |  | 3/2001 | Shen et al. |
| 7,052,795 | B2 | * | 5/2006 | McLean et al. ............... 429/34 |
| 7,060,169 | B2 | * | 6/2006 | Rohrl ........................ 204/431 |
| 2003/0118885 | A1 | * | 6/2003 | Terahara et al. .............. 429/30 |
| 2004/0134780 | A1 |  | 7/2004 | Inoue et al. |

FOREIGN PATENT DOCUMENTS

| EP | 762117 A3 | 3/1997 |
| JP | 2000-146908 A | 5/2000 |
| JP | 2002-350393 | 12/2002 |
| JP | 2003-232767 | 8/2003 |
| JP | 2005-503541 | 2/2005 |
| WO | WO 01/14864 A2 | 3/2001 |
| WO | WO 02/97420 A1 | 12/2002 |

* cited by examiner

*Primary Examiner*—Kaj K Olsen
(74) *Attorney, Agent, or Firm*—Rothwell, Figg, Ernst & Manbeck, P.C.

(57) ABSTRACT

An aqueous solution of a Na salt of a phenol sulfonic acid polymer as a liquid electrolyte is held in a separator of a liquid electrochemical gas sensor. A sensing electrode and a counter electrode are connected to the separator to detect CO at a range from about −40° C. to about 70° C.

7 Claims, 6 Drawing Sheets

LIQUID ELECTROCHEMICAL GAS SENSOR

FIELD OF THE INVENTION

The present invention relates to a liquid electrochemical gas sensor.

PRIOR ART

A gas sensor with a solid proton conductive membrane has been known (patent document 1 and 7.) In the gas sensor, the proton conductive membrane is sandwiched between a pair of electrodes and water vapor is supplied from a water reservoir. The present inventors proposed a gas sensor keeping a liquid electrolyte such as an aqueous KOH solution in a separator and supplying water vapor from a water reservoir (patent document 8.)

In gas sensors with liquid electrolytes, the liquid electrolytes are held in separators, and the electrolytes are supplied from electrolyte reservoirs via wicks. Sulfuric acid is conventionally used as the electrolyte, and hence, no metal housing may be used. A high humid atmosphere gives moisture to make sulfuric acid spill out of the liquid reservoir.

Patent document 2 proposes a liquid electrochemical gas sensor without a wick. Where, sulfuric acid is filled in a water reservoir, and moisture absorption at high humidities and dehydration at low humidities make humidity in the gas sensor almost constant. As a result, it may be prevented to dry the liquid electrolyte in the separator.

Patent document 3 proposes to fill a solution of a deliquescent salt, such as LiCl, in a water reservoir to make humidity in a gas sensor almost constant. However, sulfuric acid or the deliquescent salt makes the liquid electrolyte spill out of the water reservoir in an atmosphere at a high temperature and a high humidity.

Patent document 4 discloses a separator supporting colloidal silica and PTFE (polytetrafluoroethylene) in a paper-like glass filter. In the separator, colloidal silica provides a hydrophilic channel to keep a liquid electrolyte, and PTFE provides a hydrophobic channel to diffuse gas.

Patent document 5 discloses an $O_2$ sensor with a KOH liquid electrolyte or an $H_2SO_4$ liquid electrolyte, and that the KOH electrolyte makes the sensor characteristics drift.

Patent document 6 discloses a CO sensor with an aqueous $MgSO_4$ solution.

The liquid electrochemical gas sensor of patent document 8 works even at about −10° C., and it endures aging at about 70° C. with a highly heat resistant separator. However, this sensor has no gas sensitivity at the temperature of −40° C. In order to extend gas sensor usages from home uses to outdoor uses for recreational vehicle (RV), etc., it is required for the gas sensor to work at the temperature of −40° C. Therefore, a working range should be extend to lower temperatures. The mechanism, that the gas sensitivity of the gas sensor with KOH electrolyte is lost at −40° C., is unknown in detail, but it may be because the aqueous KOH solution is frozen and the electric conductivity of the electrolyte is reduced. Thus, a gas sensor with a liquid electrolyte other than the sulfuric acid and working at about −40° C. is desired.

Patent document 1: WO 02/097420A1
Patent document 2: WO 01/14864A1
Patent document 3: U.S. Pat. No. 5,958,200
Patent document 4: U.S. Pat. No. 4,587,003
Patent document 5: U.S. Pat. No. 5,240,893
Patent document 6: U.S. Pat. No. 5,302,274
Patent document 7: U.S. Pat. No. 6,200,443
Patent document 8: PCT/JP 2004/012258 specification

SUMMARY OF THE INVENTION

Object of the Invention

An Object of the present invention is to provide a new liquid electrochemical gas sensor with no sulfuric acid and working at a low temperature of about −40° C.

Solutions

In the invention, a liquid electrochemical gas sensor comprises a liquid electrolyte and at least a pair of electrodes connected to the electrolyte, wherein the liquid electrolyte is an aqueous electrolyte including at least one of an aromatic sulfonic acid compound, an aromatic phosphonic acid compound, an aromatic carboxylic acid compound, and a salt of these compounds.

The liquid electrolyte includes preferably at least one of an aqueous aromatic sulfonic acid and a salt thereof, more preferably at least one of an aqueous aromatic sulfonic acid polymer and the salt thereof, and most preferably an alkali metal salt of the aqueous aromatic sulfonic acid polymer. When the sensor with the aqueous electrolyte of the aqueous aromatic sulfonic acid polymer or the salt thereof is subjected to aging at a high temperature and a high humidity such as 65° C. and 95% relative humidity, the gas sensitivity at a low temperature may be maintained even after the aging.

The liquid electrolyte may be contained in a liquid reservoir and a sensing electrode, a counter electrode, and a reference electrode, etc. may be arranged in the liquid reservoir. Preferably, the liquid electrolyte is held in a porous separator and water vapor is supplied from a water reservoir to the separator. Separators, being capable of holding the aqueous liquid electrolyte, such as a filter paper and glass wool may be used, and a porous plastic separator, particularly, a hydrophilic plastic separator is preferable. For example, one hydrophilized by an alcoholic hydroxyl group, a phenol group, an amino group, an imido group, sulfonic acid group, carboxylic acid, or a salt thereof is preferable.

When, between the separator and at least one of the electrodes, a solid electrolyte membrane such as a proton conductor or a hydroxide ionic conductor is arranged, the sensitivity at the low temperature increases. For example, when an Na salt of the aromatic sulfonic acid polymer is used as the electrolyte material, an ion species migrating in the liquid electrolyte are $Na^+$ ion and $OH^-$ ion and are different from proton involving in reactions on the sensing electrode. Where, for example, when the proton conductor membrane is positioned between the separator and the electrode, it is presumed that the proton generated by oxidation of CO is injected into the liquid electrolyte; corresponding to this, $OH^-$ ion migrates to the sensing electrode, and $Na^+$ ion migrates to the counter electrode. It is presumed that, in an interface between the proton conductor in the counter electrode and the liquid electrolyte, the reaction of $H_2O \rightarrow H^+ + OH^-$ occurs; the resultant $H^+$ migrates to the proton conductor in the counter electrode, and $OH^-$ migrates to the liquid electrolyte. In place of the proton conductor, a hydroxyl ionic conductor may be used. These solid electrolytes may be contained in the sensing electrode or the counter electrode. In this case, the solid electrolyte membrane is not necessary.

Preferably, a narrowed part is made between an opening and a bottom of a metal can, a metal washer having an opening is supported by the narrowed part, and the separator and the at least one pair of electrodes are arranged on the metal washer, Water is provided between the metal washer and bottom of the metal can, and water vapor is supplied from the opening of the metal washer to the separator.

The electrodes comprise, for example, a sensing electrode and a counter electrode. The counter electrode may be a noble metal electrode. However, an oxide or a hydroxide of at least one of Mn, Ni, Pb, and Zn may be used as the counter electrode. The counter electrode is cost effective and works in an atmosphere without oxygen.

Advantages in the Invention

The present invention gives the following advantages.
(1) Sulfuric acid is not used as the liquid electrolyte and, therefore, sulfuric acid does not spill out in a high humidity atmosphere.
(2) The gas sensitivity is obtained at the low temperature such as about −40° C., and therefore, the gas sensor may be used for outdoor uses such as for RV usage.
(3) The aromatic sulfonic acid polymer and its salt result in the stable sensitivity at the lower temperatures such as −40° C., even after a high temperature and high humidity atmosphere is experienced.

DESCRIPTION OF THE REFERENCE NUMERALS

Figure 1:
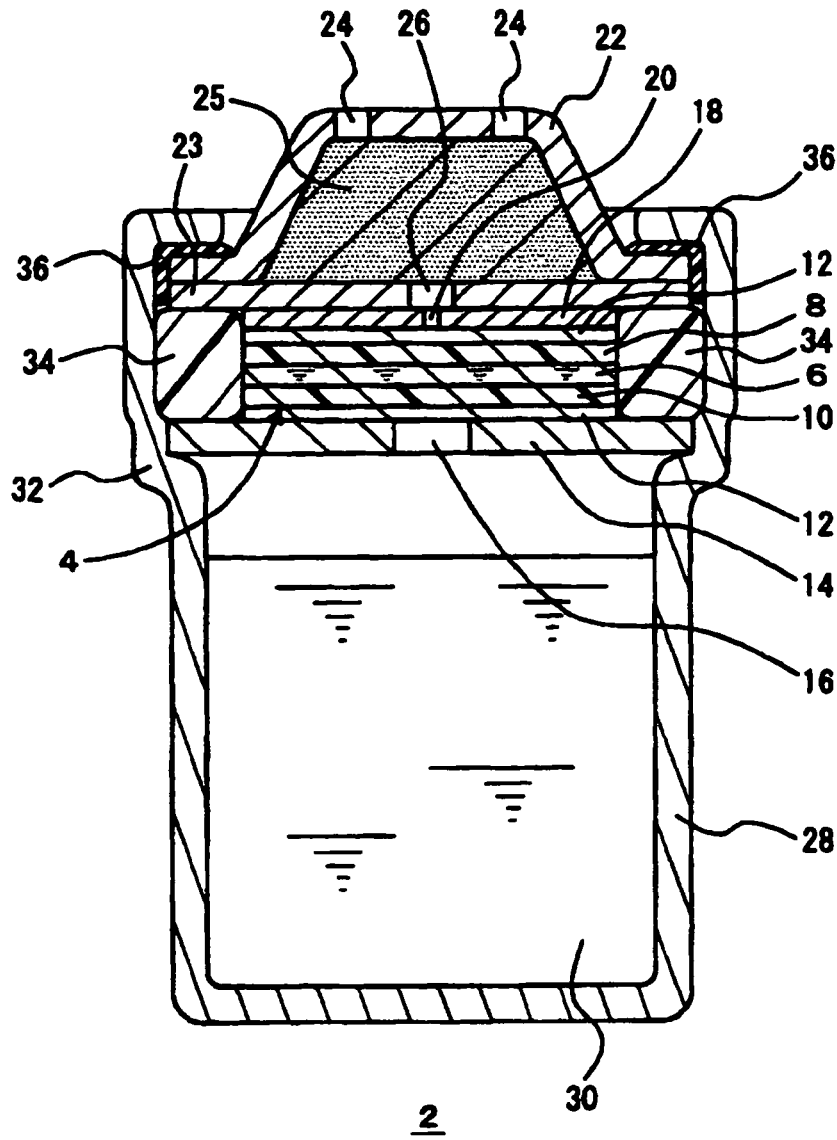
FIG. 1 is a sectional view of the liquid electrochemical gas sensor according to an embodiment.

2 Liquid electrochemical gas sensor
4 Sensor body
6 Separator
8 Sensing electrode
10 Counter electrode
12 Hydrophobic conducive membrane
14 Washer
16 Water vapor introducing hole
18 Diffusion control plate
20 Diffusion control hole
22 Cap
23 Bottom plate
24, 26 Openings
25 Filter
28 Metal can
30 Water
32 Narrowed part
34 Adhesive ring
36 Sealing material
38 Electron conductive electrode
40 Solid electrolyte membrane
42 Mixed conductive electrode

BEST EMBODIMENT OF THE INVENTION

The best embodiment of the present invention will be described below for practice.

Embodiment

FIG. 1 to FIG. 17 show the embodiments and the modification. In FIG. 1, 2 denotes a liquid electrochemical gas sensor, 4 denotes a sensor body, and a sensing electrode 8 and a counter electrode 10 are mounted on front and rear sides of a separator 6. The separator 6 is porous and holds a liquid electrolyte and has a thickness of about 0.1 mm and a diameter of about 5 to 20 mm, for example. The separator 6 is, for example, made of a woven cloth or unwoven cloth of a synthetic fiber and hydrophilized by introducing a sulfonic acid group or an alcoholic hydroxide group. Hereafter, the embodiment with a porous plastic separator introduced with the alcoholic hydroxide group will be described.

The sensing electrode 8 comprises, for example, a mixture of Pt-supported carbon black and PTFE (polytetrafluoroethylene) binder. Pt—$RuO_2$, Pd, or other proper catalysts for electrodes may be used in place of Pt. The composition of the counter electrode 10 is the same as that of the sensing electrode 8. 12 is a hydrophobic conductive membrane, 14 is a metal washer made of SUS, etc. 16 is a water vapor introducing hole having a diameter ranging approximately from 1 to 3 mm, for example, and 18 is a diffusion control plate made of a metal thin plate such as SUS having the thickness of about 100 μm and has a diffusion control hole 20 having the diameter of about 0.1 mm. Preparing the diffusion control hole 20 into the thin diffusion control plate 18 makes the pore size of the diffusion control hole 20 constant and the unevenness of the gas sensitivity small. 22 is a metal cap, 23 is a bottom plate thereof, 24 and 26 are openings for introducing a gas, 25 is a filter made of activated coal, silica gel, or zeolite, etc.

28 is a metal can made of SUS, of which lower part contains water 30 such as pure water or gelled water. 32 is a narrowed part for supporting the washer 14 on the top thereof, 34 is an adhesive ring made of an adhesive urethane elastomer sealing the surrounding of the sensor body 4 to prevent invasion of water from a side of the sensor body 4. 36 is a insulative sealing material, which may be a sealing tape, for sealing by insulating the metal can 28 from the cap 22 to prevent invasion of the gas. The top of metal can 28 is caulked to the cap 22. As the result, the sensing electrode 8 is electrically communicated with the cap 22 and the counter electrode 10 is electrically communicated with the metal can 28 to prevent leaking water and invasion of the gas from a channel other than the diffusion control hole 20. Liquid water reaching the hydrophobic conductive membrane 12 from the water vapor introducing hole 16 is blocked by hydrophobic conducive membrane 12.

Figure 2:
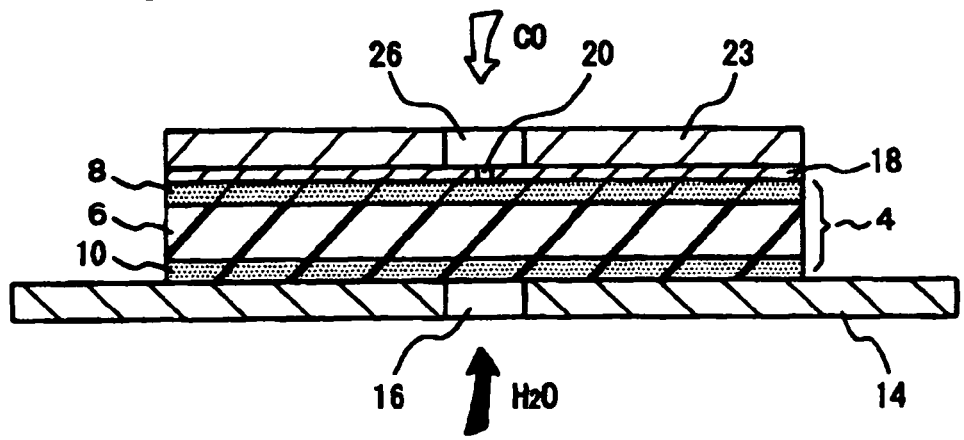
FIG. 2 is the sectional view showing a main body of the sensor and its surrounding area of the liquid electrochemical gas sensor according to the embodiment.
Figure 3:
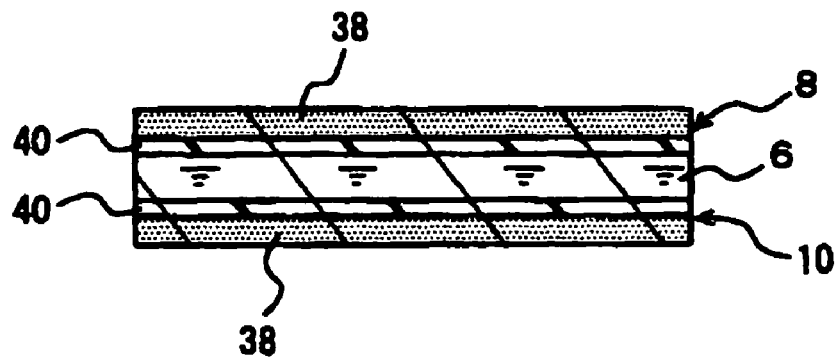
FIG. 3 is the sectional view showing the main body of the sensor and its surrounding area of the liquid electrochemical gas sensor according to the embodiment.
Figure 4:
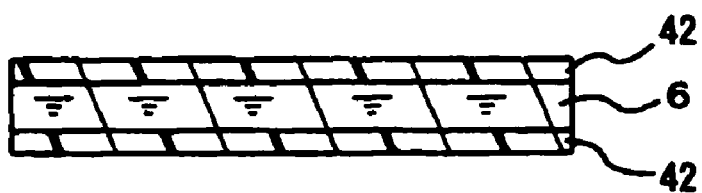
FIG. 4 is the sectional view showing the main body of the sensor and its surrounding area of the liquid electrochemical gas sensor according to a modification.

FIG. 2 shows the supply of water vapor and CO to be detected. In order to achieve sensitivity to CO and $H_2$ at a low temperature, the species of the liquid electrolyte is definitely important. In addition to this, in order to achieve gas sensitivity, it is preferable to contact the solid electrolyte to electrodes 8 and 10. In FIG. 3, a solid electrolyte membrane 40, which comprises a proton conductive polymer or a solid hydroxide ionic conductor having a basic group such as pyridine to the side chain, is arranged between an electron conductive electrode 38 such as Pt-C-PTFE and the separator 6. In the embodiment, the structure of FIG. 3 is employed and a proton conductive polymer membrane is used. Without the solid electrolyte membrane 40, the sensitivity at −40° C. showed a several-fold decrease. In addition, as shown in FIG. 4, Pt-C-PTFE may be blended with the proton conductive polymer or the solid hydroxide ionic conductor to prepare a mixed conductive electrode 42. In the embodiment, the sensor has two electrodes, the sensing electrode and the counter electrode; however, a reference electrode may be installed as the third electrode.

The counter electrode 10 may be constituted by an oxidation agent made of a metal oxide or a metal hydroxide (active material). In this case, the counter electrode 10 is, for example, $MnO_2$, $NiO(OH)$, $PbO_2$, or $ZnO$ supported on a porous carbon paper with PTFE binder. Hydroxide ion is produced on the counter electrode 10 by reactions such as the followings, or proton produced on the sensing electrode 8 is consumed.

$$MnO_2 + 2H_2O + 2e^- \rightarrow Mn(OH)_2 + 2OH^- \quad (1)$$

$$MnO_2 + 2H^+ + 2e^- \rightarrow Mn(OH)_2 \quad (2)$$

$$NiO(OH) + H^+ + e^- \rightarrow Ni(OH)_2 \quad (3)$$

$$PbO_2 + 2H^+ + 2e^- \rightarrow PbO + H_2O \quad (4)$$

The electrolyte supported in the separator 6 is preferably an aqueous electrolyte of aromatic sulfonic acid, aromatic phosphonic acid, aromatic carboxylic acid, or a salt of these compounds. The salt is preferably an alkali metal salt such as an Na salt; the aromatic sulfonic acid polymer or alkali metal salt thereof is particularly preferable. An aqueous electrolyte may contain, for example, the third component such as starch or glycerin, in addition to the alkali metal salt of the aromatic sulfonic acid polymer and water. The concentration of the electrolyte material in the liquid electrolyte may change with a relative humidity; however, for example, it is 0.3 to 30 wt %, and is preferably 1 to 20 wt %.

Figure 5:
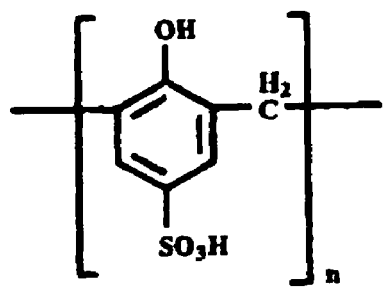
FIG. 5 shows a chemical formula of PSR (o-cresol-4 sulfonic acid polymer) as the electrolyte material used in the embodiment.

FIG. 5 shows a chemical formula of the electrolyte material, PSR, used in the embodiment. The correct material name is o-cresol-4-sulfonic acid polymer, the molecular weight is, for example, 10000 to 40000, more widely, for example, 10000 to 100000. PSR is preferably used as the Na salt and soluble with water in an arbitrary proportion in an acid type and a salt type thereof. The acid type is a weak acid material, its pH is about 2 in 30 wt % aqueous solution, for example, and the salt type is a weak alkali material. There are many materials similar thereto, and a hydrogen atom of a benzene ring and a methylene group, for example, may be substituted by other groups. On the other hand, a phenolic hydroxyl group of PSR adsorbs well to the hydroxyl group in a plastic separator, resulting in good retention of the electrolyte substance in the separator. In a large n value, the electrolyte is difficult to migrate and the adhesion to the separator increases to cause the increase in durability against high temperature and high humidity atmospheres.

Figure 6:
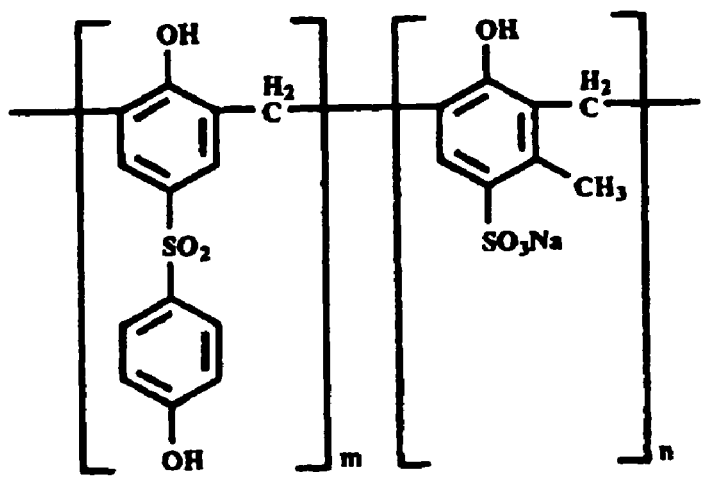
FIG. 6 shows the chemical formula of BS-PSR (copolymer of bisphenol $SO_2$ and 2,3-xylenol-4-sulfonic acid) as the electrolyte material used in the embodiment.

The material BS-PSR in FIG. 6 may be regarded as a derivative of PSR in FIG. 5 and a bisphenol group in FIG. 6 has a role for increasing adhesion to the separator. It is preferable that n is made larger than m, the PSR group works as the electrolyte, and the bisphenol group works for increasing the adhesion to the separator.

Figure 7:
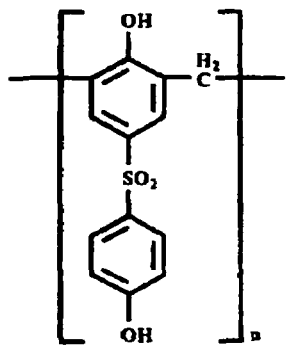
FIG. 7 shows the chemical formula of BSR (bisphenol $SO_2$ polymer) as the electrolyte material used in a comparative example.
Figure 8:
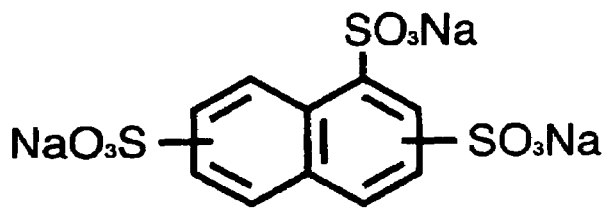
FIG. 8 shows the chemical formula of a Na salt form NTS (naphthalene trisulfonic acid) as the electrolyte material used in the embodiment.

FIG. 7 shows BSR (bisphenol $SO_2$ polymer.) When 10 wt % aqueous solution of this material is held in the separator, the CO sensitivity did not occur at −40° C. In FIG. 8, NTS (Na salt of naphthalene trisulfonic acid) is used as the example of the material containing a large number of sulfonic acid groups. When an aqueous solution of this material is held in the separator, the CO sensitivity occured at −40° C. However, when aging was carried out at 65° C. and RH 95% for 7 weeks, the response to CO became worse at −40° C. The difference between the materials of FIGS. 5 and 6 and the material of FIG. 8 is primarily whether the materials are in polymer or not. The secondary difference is whether the material contains a group which strongly adsorbs to hydroxyl groups, etc. in the separator. It is presumed that in combination of these two factors, NTS used in FIG. 8 causes relatively weak adhesion to the separator and, thus, NTS removes from the separator by the high temperature and high humidity atmosphere. Materials similar to the aromatic sulfonic acid includes the aromatic phosphonic acid, the aromatic carboxylic acid, and the like, which are weaker acids than the aromatic sulfonic acid, may be used as the electrolyte material with increasing the acid strength by a substituent. The Na salts of the aromatic phosphonic acid, the aromatic carboxylic acid, or the like may be also used as the alkaline electrolyte.

In conclusion, the sensitivity at −40° C. is preferably realized with the aromatic sulfonic acid, the aromatic phosphonic acid, the aromatic carboxylic acid, or the salt of these compounds. In addition, in order to keep the sensitivity at −40° C. after experiencing in the high temperature and high humidity atmosphere, polymers of these compounds are preferable. The electrolyte material has preferably a functional group such as the hydroxyl group or the like, easily adhering to a plastic.

Figure 9:
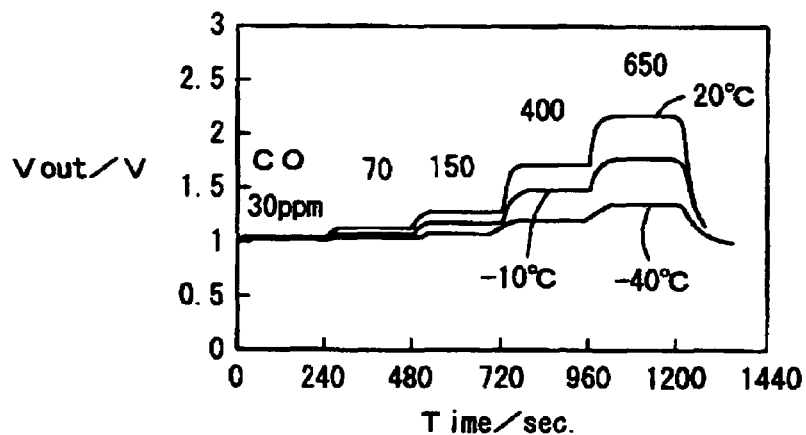
FIG. 9 shows characteristics of the embodiment with 3 wt % PSR and a response before an endurance test to 30 ppm, 70 ppm, 150 ppm, 400 ppm, and 650 ppm of CO at −40° C., −10° C., and 20° C.

FIG. 9 and following figures show the response to CO at 20° C., −10° C., and −40° C. The data is an output waveform from an each single sensor. The measurement is operated by a plurality of sensors and representative waveforms thereof are illustrated. Three lines in each figure represent data at 20° C., −10° C., and −40° C. in the order from the top to the bottom. The measured CO gas are 30 ppm, 70 ppm, 150 ppm, 400 ppm, and 650 ppm in the order and is replaced with clean air after 650 ppm.

Figure 10:
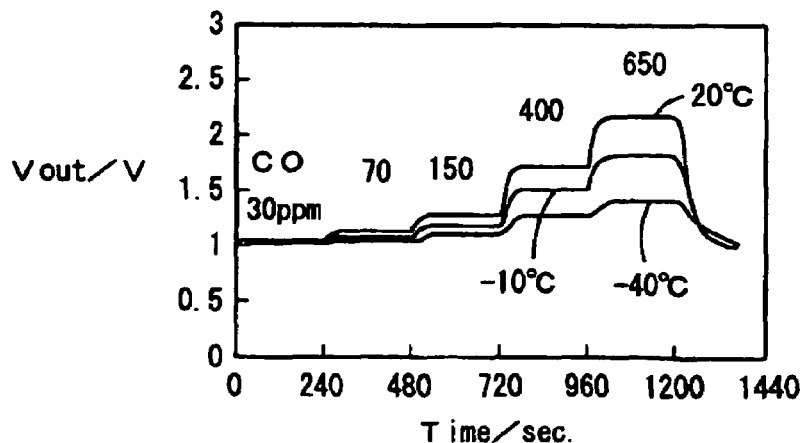
FIG. 10 shows characteristics of the same sample as that of FIG. 9 after endurance at 70° C. for 7 weeks.
Figure 11:
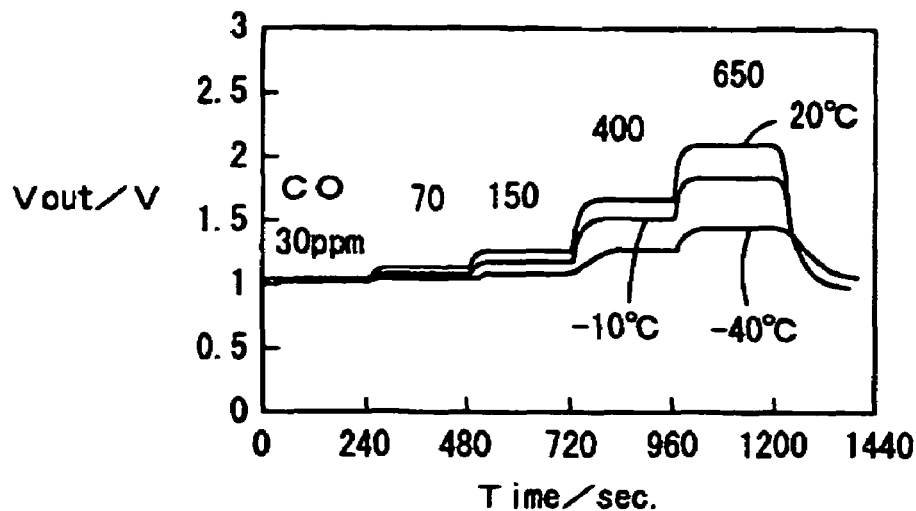
FIG. 11 shows characteristics of the same sample as that of FIG. 9 after endurance at 65° C. and RH 95% for 7 weeks.
Figure 12:
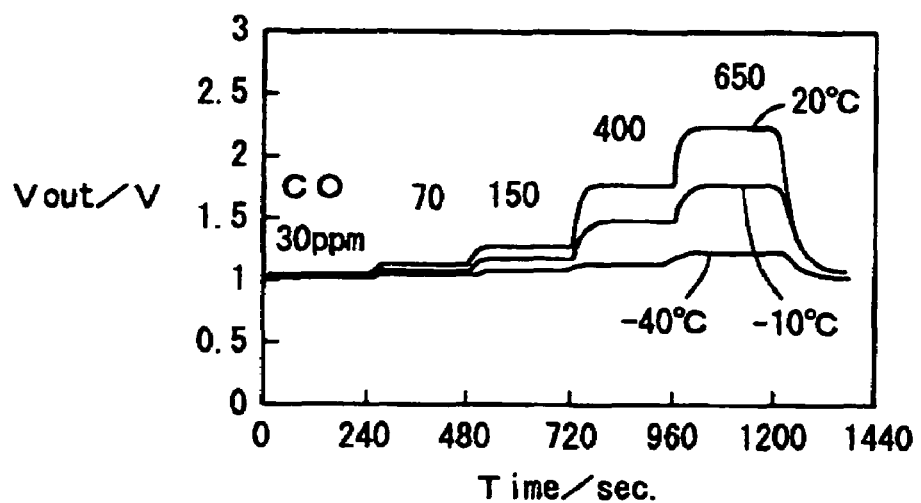
FIG. 12 shows characteristics of the embodiment with 10 wt % PSR and the response before the endurance test against 30 ppm, 70 ppm, 150 ppm, 400 ppm, and 650 ppm of CO at −40° C., −10° C., and 20° C.

FIG. 9 to FIG. 11 show the results of the sensor with an aqueous solution of 3 wt % Na salt of PSR as the electrolyte and a fluorine resin membrane hydrophilized by the alcoholic hydroxyl group as the separator. FIG. 9 shows the result before aging, and FIG. 10 shows the result after aging in the atmosphere at 70° C. for 7 weeks without controlling the relative humidity. FIG. 11 shows the result after aging at 65° C. and RH 95% for 7 weeks. The gas sensitivity decreases at a lower temperature, however, a sufficiently quick response is observed at −40° C., and the temperature dependency is one which may be compensated with a thermistor. As shown in FIG. 10 and FIG. 11, experiences of the high temperature atmosphere or the high temperature and high humidity atmosphere presents no significant difference in the response to CO at −40° C. By the way, this sensor works at 70° C. and a hydrogen sensitivity is, in general, about a half of the CO sensitivity. FIG. 12 shows the characteristics of a sensor with 10 wt % aqueous PSR solution, where PSR is the Na salt type. The data of FIG. 12 was taken before the aging, and the endurance test at 70° C. and 65° C. ×95% RH caused no change. However, the CO sensitivity at −40° C. is somewhat smaller than that of FIG. 11. The reason why a PSR concentration has an optimal value is unknown.

Figure 13:
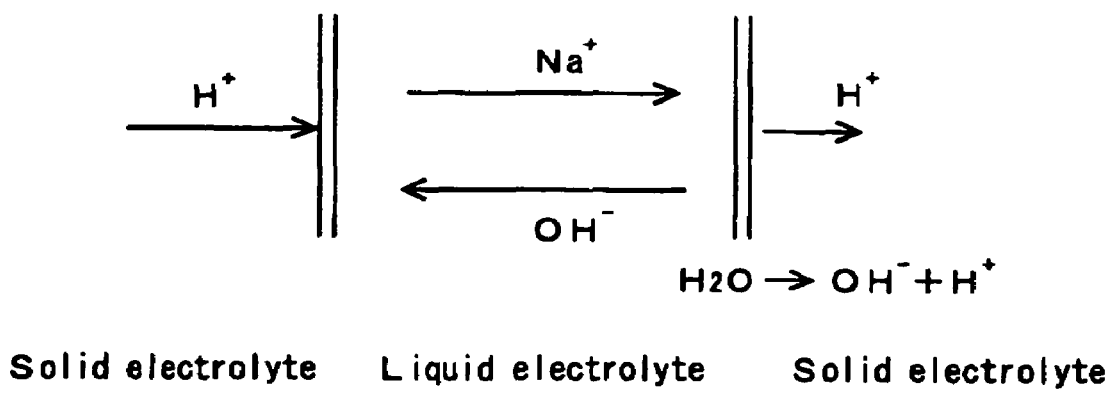
FIG. 13 is a schematic view of an ion migration in the embodiment with an Na salt type PSR.

FIG. 13 shows the schematic view of the ion migration in the Na salt type PSR liquid electrolyte. When the reaction of CO with water generates $CO_2$, proton, and electron in the sensing electrode, the proton is injected from the proton conductive membrane into the liquid electrolyte. It is presumed that, in the liquid electrolyte, then, the Na ion migrates to the counter electrode and a hydroxyl ion migrates toward an interface with the proton conductive membrane in the sensing electrode. It is presumed that, on an interface with the proton conductive membrane in the counter electrode, water is dissociated to hydroxyl ion and proton and the dissociated proton flows into the proton conductive membrane, and the hydroxyl ion migrates in the liquid electrolyte.

Figure 14:
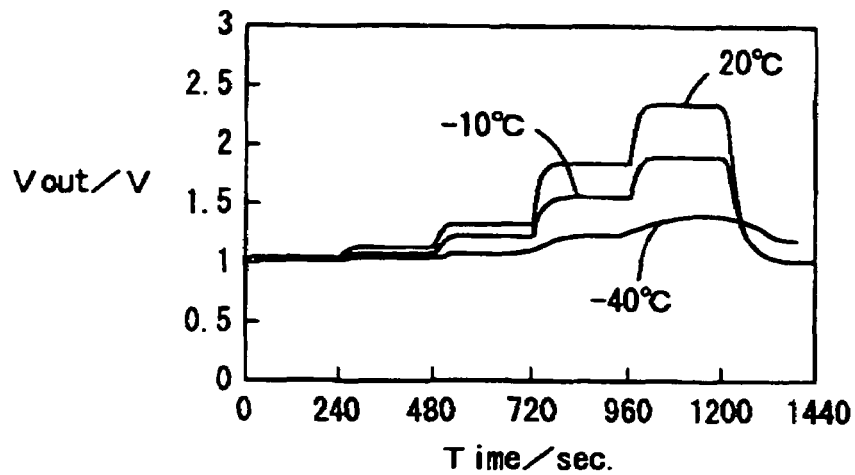
FIG. 14 shows characteristics of the embodiment with 2 wt % NTS and the response before the endurance test against 30 ppm, 70 ppm, 150 ppm, 400 ppm, and 650 ppm of CO at −40° C., −10° C., and 20° C.
Figure 15:
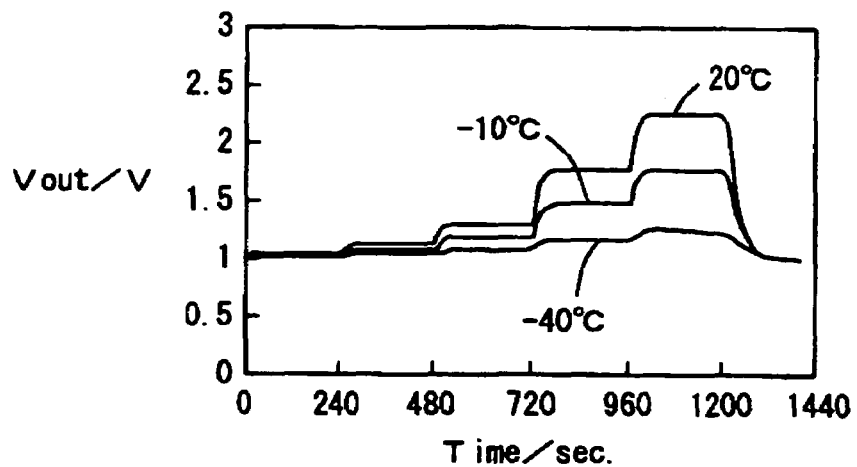
FIG. 15 shows characteristics of the same sample as that of FIG. 14 after endurance at 70° C. for 7 weeks.
Figure 16:
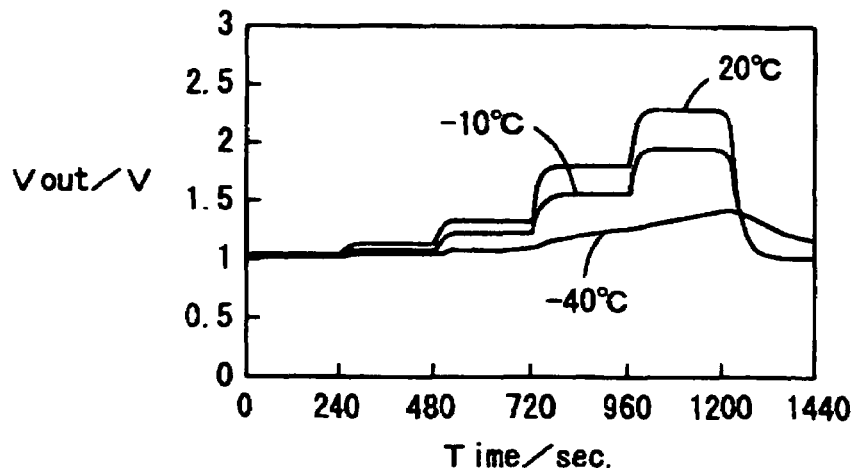
FIG. 16 shows characteristics of the same sample as that of FIG. 14 after endurance at 65° C. and RH 95% for 7 weeks.

FIG. 14 to FIG. 16 show the result when an aqueous 2 wt % NTS solution is used. FIG. 14 shows the result before the aging and the CO sensitivity occurs at −40° C., however, the response is slow in comparison with PSR. FIG. 15 shows the result after the aging at 70° C. for 7 weeks, CO sensitivity reduces somewhat at −40° C. and the response is slightly improved. FIG. 16 shows the result after endurance at 65° C. and RH 95% for 7 weeks, and the response at −40° C. becomes unclear. These results suggest that the non-polymer aromatic sulfonic acid compound without the hydroxyl group contributing to increasing the adhesion to the separator caused escape of the electrolyte from the separator in the high temperature and high humidity atmosphere.

Figure 17:
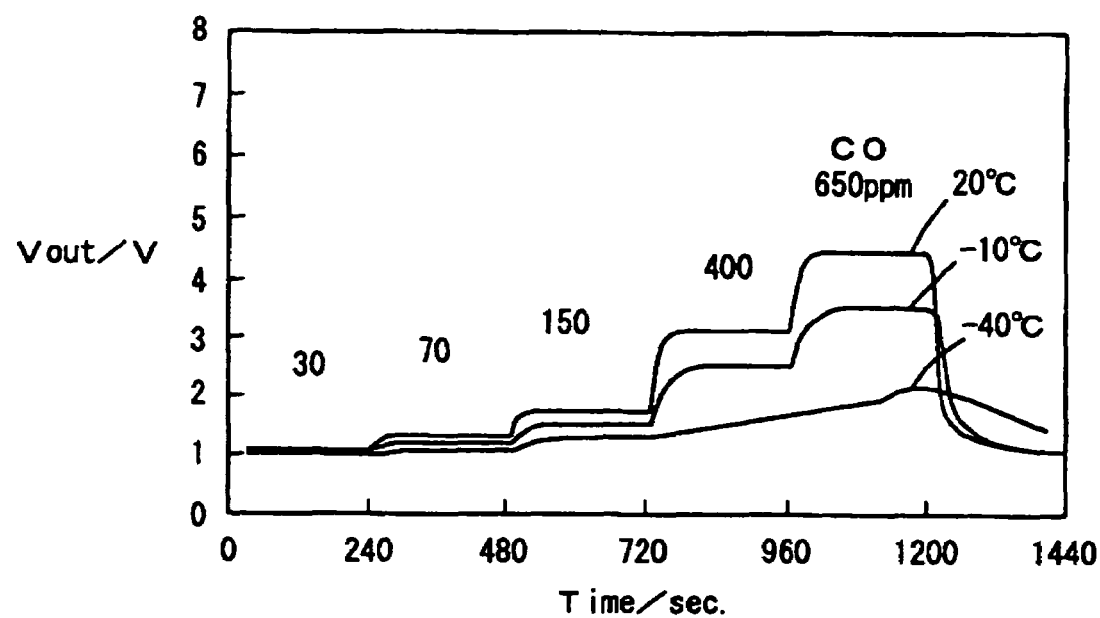
FIG. 17 shows characteristics of a comparative example with an aqueous 0.1 N-KOH solution and the response before the endurance test to 30 ppm, 70 ppm, 150 ppm, 400 ppm, and 650 ppm of CO at −40° C., −10° C., and 20° C.

FIG. 17 shows the CO sensitivity of a 0.1N aqueous KOH solution, and the data is taken before the aging. A sufficient sensitivity is kept up to −10° C., however, the response of CO to −40° C. is unclear.

Generation mechanisms of the CO sensitivity at −40° C. is analyzed on the basis of these facts. In case of the aqueous KOH solution, the electrolyte is frozen at −40° C., and the ion migration is inhibited. On the contrary, in case of the aromatic sulfonic acids and the salts thereof, they are relatively large molecules and have hydrophilic sulfonic acid group and hydrophobic benzene ring to inhibit to produce a eutectic. Therefore, it is presumed that cooling the electrolyte to about −40° C. freezes locally water, materials such as PSR aggregates on a surface of a fiber or a pore in the separator, so that the materials are kept as a liquid with a small amount of water without crystallization.

Next, the polymer electrolyte and the functional group in the electrolyte such as hydroxyl group determine the endurance of the gas sensor against the high temperature atmosphere, and the high temperature and high humidity atmospheres. The electrolyte having a large molecular weight and the functional group such as the hydroxyl group easily adheres to the separator, and when the liquid electrolyte contact to water condensed on the surrounding of the separator in a condition of the high temperature and high humidity, the electrolyte material attaches easily to the separator.

The invention claimed is:

1. A liquid electrochemical gas sensor comprising a liquid electrolyte and at least a pair of electrodes connected to the electrolyte, wherein said liquid electrolyte is an aqueous electrolyte including at least one of an aromatic sulfonic acid polymer and a salt thereof.

2. A liquid electrochemical gas sensor according to claim 1, wherein said liquid electrolyte is retained in a porous separator and water vapor is supplied from a water reservoir to said separator.

3. A liquid electrochemical gas sensor according to claim 2, wherein a solid electrolyte membrane is arranged between the separator and at least one of the electrodes.

4. A liquid electrochemical gas sensor according to claim 2, wherein a narrowed part is made between an opening and a bottom of a metal can, a metal washer having an opening is supported by said narrowed part, said separator and said at least a pair of electrodes are arranged on the metal washer, and water is contained between the metal washer and the bottom of the metal can to supply water vapor from the opening of the metal washer to the separator.

5. A liquid electrochemical gas sensor according to claim 2, wherein the liquid electrolyte is an aqueous electrolyte including an alkali metal salt of the water-soluble aromatic sulfonic acid polymer.

6. A liquid electrochemical gas sensor according to claim 2, wherein said separator is made of a porous plastic.

7. A liquid electrochemical gas sensor according to claim 1, wherein said at least a pair of electrodes comprise a sensing electrode and a counter electrode, and the counter electrode is an oxide or a hydroxide of at least one of Mn, Ni, Pb, and Zn.

* * * * *